United States Patent
Rajasekharan et al.

(10) Patent No.: US 11,796,549 B2
(45) Date of Patent: Oct. 24, 2023

(54) REAL-TIME MANAGEMENT OF ANALYTE RECOVERY

(71) Applicant: Hach Company, Loveland, CO (US)

(72) Inventors: Vishnu Vardhanan Rajasekharan, Fort Collins, CO (US); Cary Burton Jackson, Fort Collins, CO (US); Russell Young, Fort Collins, CO (US)

(73) Assignee: Hach Company, Loveland, CO (US)

( * ) Notice: Subject to any disclaimer, the term of this patent is extended or adjusted under 35 U.S.C. 154(b) by 315 days.

(21) Appl. No.: 17/174,972

(22) Filed: Feb. 12, 2021

(65) Prior Publication Data
US 2022/0260599 A1    Aug. 18, 2022

(51) Int. Cl.
*G01N 35/00*    (2006.01)

(52) U.S. Cl.
CPC .......... *G01N 35/00663* (2013.01); *G01N 2035/00673* (2013.01)

(58) Field of Classification Search
CPC .......... G01N 35/00663; G01N 2035/00673
See application file for complete search history.

(56) References Cited

U.S. PATENT DOCUMENTS

2014/0273052 A1   9/2014  Reddy et al.
2019/0325992 A1*  10/2019 Aigner .............. G01N 33/66

FOREIGN PATENT DOCUMENTS

WO      2010142004 A2    12/2010
WO   WO-2013160424 A1 * 10/2013 ............. G01D 18/00

* cited by examiner

*Primary Examiner* — Jennifer Wecker
*Assistant Examiner* — Kathryn Elizabeth Limbaugh
(74) *Attorney, Agent, or Firm* — Ference & Associates

(57) ABSTRACT

An embodiment provides a method for real-time management of analyte recovery within a system for measuring at least one parameter of a fluid within the system by monitoring signals from the system against a set of conditions, the method including: receiving, from the system, signals providing information regarding the system, wherein the system includes at least one reagent flowing into the system and recovers analytes within the fluid, wherein the analytes provide an indication of a value of the at least one parameter; identifying, by analyzing the signals, whether the analyte recovery of the system is meeting the set of conditions identifying a desired analyte recovery of the system; and modifying, based upon the analyte recovery not meeting the set of conditions, conditions of the system for recovery of the analyte, wherein the modifying includes adjusting at least one parameter of the system.

20 Claims, 3 Drawing Sheets

REAL-TIME MANAGEMENT OF ANALYTE RECOVERY

FIELD

This application relates generally to systems for measuring parameters in a fluid, and, more particularly, to real-time management of analyte recovery within a system.

BACKGROUND

Ensuring water quality is critical in a number of industries such as pharmaceuticals and other manufacturing fields. Additionally, ensuring water quality is critical to the health and well-being of humans, animals, and plants which are reliant on the water for survival. To determine the water quality, different parameters of the water are measured. Similarly, devices or systems can be utilized to measure different parameters of any fluid. Since different devices may measure different parameters, the measurement data from each of the devices is combined in order to determine the overall quality or other multi-parameter measurements or values regarding the fluid.

BRIEF SUMMARY

One embodiment provides a method for real-time management of analyte recovery within a system for measuring at least one parameter of a fluid within the system by monitoring signals from the system against a set of conditions, the method including: receiving, from the system, signals providing information regarding the system, wherein the system includes at least one reagent flowing into the system and recovers analytes within the fluid, wherein the analytes provide an indication of a value of the at least one parameter; identifying, by analyzing the signals, whether the analyte recovery of the system is meeting the set of conditions identifying a desired analyte recovery of the system; and modifying, based upon the analyte recovery not meeting the set of conditions, conditions of the system for recovery of the analyte, wherein the modifying includes adjusting at least one parameter of the system.

Another embodiment provides a system for real-time management of analyte recovery within a system for measuring at least one parameter of a fluid within the system by monitoring signals from the system against a set of conditions, the system including: at least one reagent flowing into the system; a memory storing instructions executable by a processor to: receive, from the system, signals providing information regarding the system, wherein the system recovers analytes within the fluid, wherein the analytes provide an indication of a value of the at least one parameter; identify, by analyzing the signals, whether the analyte recovery of the system is meeting the set of conditions identifying a desired analyte recovery of the system; and modify, based upon the analyte recovery not meeting the set of conditions, conditions of the system for recovery of the analyte, wherein the modifying includes adjusting at least one parameter of the system.

A further embodiment provides a computer program product for real-time management of analyte recovery within a system for measuring at least one parameter of a fluid within the system by monitoring signals from the system against a set of conditions, the computer program product including: a storage device having code stored therewith, the code being executable by the processor and including: code that receives, from the system, signals providing information regarding the system, wherein the system recovers analytes within the fluid, wherein the analytes provide an indication of a value of the at least one parameter; code that identifies, by analyzing the signals, whether the analyte recovery of the system is meeting the set of conditions identifying a desired analyte recovery of the system; and code that modifies, based upon the analyte recovery not meeting the set of conditions, conditions of the system for recovery of the analyte, wherein the modifying includes adjusting at least one parameter of the system.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
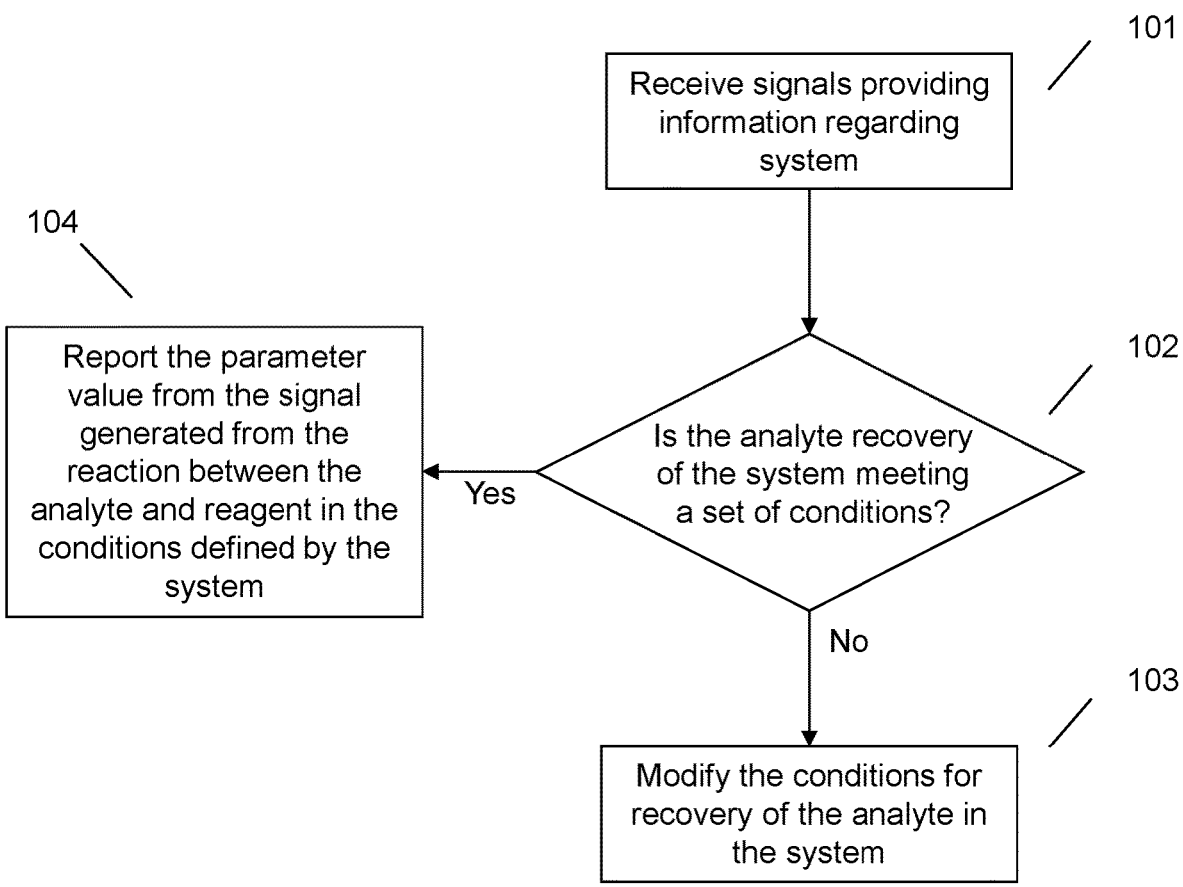
FIG. 1 illustrates example method for real-time management of analyte recovery within a system for measuring at least one parameter of a fluid within the system by monitoring signals from the system against a set of conditions.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Devices are used to measure parameters of fluids. For example, the fluid may run through a cabinet or box, referred to as a system herein for ease of readability, and different parameters impacting the fluid quality can be measured using the system. In some cases multiple parameters impacting the fluid quality may be measured. Alternatively, the system may measure a single parameter of the fluid. To assist in measuring the parameter, the system utilizes one or more reagents that are added to the fluid in order to produce measurable entities that result in signals corresponding to the analytes within the fluid. The analytes are measured and can be correlated to values of parameters within the fluid. This type of system is that the system is generally used to measure more than one analyte, even in the event that a single parameter of the fluid is being measured. To measure more than one analyte, the system generally utilizes more than one reagent, with each reagent corresponding to one of the analytes being measured. Within the system the volumes of reagents are generally the same, kept at the same pressure, same temperature, and the like.

While the idea behind such a system is to be able to achieve the best recovery of all of the analytes that are being measured, this generally does not occur. Rather, the recovery of one analyte within the fluid may be better than the recovery of another analyte within the fluid. There are various reasons that the recovery of one analyte may be compromised. For example, the reactions between the reagents and the fluid and/or analytes in the fluid may cause by-products, intermediate products, or the like, that interfere with the reaction of other reagents with analytes in the fluid. As another example, different reagents and/or analytes may cause side reactions, interactions between the analytes, and/or the like, which compromise the performance of the recovery of one analyte over another. Conventionally there is not a technique or system that can account for the imbalance in analyte recovery.

Accordingly, an embodiment provides a system and method for real-time management of analyte recovery within a system for measuring at least one parameter of a fluid within the system by monitoring signals from the system against a set of conditions. The system receives signals from the system that provide information regarding the system. For example, the signals may identify a reagent consumption, system temperature, cell condition, analytes, signal growth rate, and the like. From the signals the system can determine if the analyte recovery of the system is meeting a set of conditions that indicate whether there is an imbalance in the analyte recovery of the system. If there is an imbalance in the analyte recovery, the system can modify the operating condition or a parameter of the system, for example, an attribute of one or more of the reagents, a variable of the system, or the like, in order to correct the imbalance in the analyte recovery.

Thus, the described system and method provides a technique to account for an imbalance in analyte recovery in a system, which is not possible using conventional techniques. Additionally, the system monitors the analyte recovery as the analyte recovery is being performed so that modifications can be made to the system in real-time. This prevents inaccurate or compromised recovery of analytes within the fluid. Since the analyte recovery is no longer compromised or inaccurate, the described system and method provides more accurate measurements of the desired parameters of the fluid.

The illustrated example embodiments will be best understood by reference to the figures. The following description is intended only by way of example, and simply illustrates certain example embodiments.

FIG. 1 illustrates an example for real-time management of analyte recovery within a system for measuring at least one parameter of a fluid within the system by monitoring signals from the system against a set of conditions. At 101 the system receives signals from a system that measures at least one parameter of a fluid that is introduced to the system. The system includes at least one reagent that is introduced to the fluid in order to generate signals arising from the reaction between the reagents and the analytes that can be measured and then correlated to at least one parameter. For example, the system may be a colorimetric system that uses reagents that cause a colorimetric change in a fluid. By way of example only, some suitable analytes include (1) N, N Diethyl-p-phenylenediamine free radical (Magenta colored Wursters dye formation by the reaction of the DPD reagent and parameter chlorine), (2) vanado molybdo phosphoric acid (Yellow color, inorganic complex formation by the reaction of the Molybdo vanadate reagent and parameter phosphorus), (3) chromotropic acid diazonium salt (Pink colored complex formation by the reaction of sulfanilic acid reagent and nitrite parameter. (4) Carbon dioxide (Formed by the reaction between ozone, Manganese reagents and organic carbon parameter), (5) Nitrate (Formed by the reaction between Ozone, Manganese reagents and total nitrogen parameter), and the like.

The system can measure the change in color or provide an optical signal either in infrared or ultraviolet regions of the electromagnetic spectrum (i.e., the analyte in this example) which can be correlated to a measurement of a parameter in the fluid, for example, chlorine, nitrogen, or the like. By way of example only, other suitable parameters may include phosphate, chlorine, nitrite, Total organic carbon, Total nitrogen, and the like. To aid in understanding, an analyte is compound that is formed by the reaction between the parameter that is desired to be determined and the reagent. The parameter is the final determinant that provides value to the customer which needs to be converted to an analyte in an analytical procedure that involves chemical reactions due to the lack of physical scientific methods to determine the parameter by itself without any reagents or chemical reactions. Thus, the system recovers analytes within the fluid from the signal(s) that are produced from a reaction between the reagent(s) and parameters within the fluid. The analyte(s) can be measured which can then be correlated to a value of the parameter. Thus, the analyte(s) that are recovered provide an indication of a value of one or more parameters within the fluid.

As an example use case that will be referred to throughout this disclosure, the system may be a system that measures Total Nitrogen and Total organic carbon (TN and TOC) parameters within a fluid at the same time. In a traditional system, the simultaneous oxidation of nitrogenous and carbonaceous compounds in a single reactor cell causes sub optimal recovery due to cross reactions, reaction conditions (e.g., reagents, time, temperature, etc.) that are not optimized for efficient recovery for both compounds simultaneously, kinetics and thermodynamics for the oxidation of the compounds are different (e.g., hydroxyl radical oxidation of nitrogen compounds are in general slower than carbonaceous compounds), a loss of oxidized nitrogen compounds as gaseous products ($N_xO_Y$ gases) after oxidation due to sub-optimal oxidation conditions causes lower recoveries, and the like. The described system attempts to overcome these problems to allow for optimal recovery of both parameters simultaneously using the system and method described herein.

The signals that are received at 101 may include signals that provide an indication regarding any portion of the system that may provide an indication of how the system is functioning, reagent use, and/or analyte measurement values. Stated differently the signals that are received at 101 may include any signals that provide an indication of the analyte recovery of the system. For example, the signals may provide an indication regarding attributes within the system, for example, reagent consumption, system temperature, cell condition, the analytes being measured, signal growth rate, and the like. As another example, the signals may provide an indication regarding feedback from the system, for example, reagent delivery rate, reagent delivery amount, temperature ramp, reagent concentrations, and the like. As a final, non-limiting example, the signals may provide an indication regarding either the reagent and/or analytes, for example, analyte measurement values, historical reagent volumes correlated with historical analyte values, and the like. Using the TN and TOC example, the signals may provide an indication of reagents being consumed in the recovery of TN and TOC (which may be measured based upon $N_2$ and C), the temperature of the system during recovery, a historical measurement value corresponding to both the TN and TOC values and the conditions of the system resulting in those measurement values, reagent delivery rates for each of the TN and TOC recoveries, and the like.

At 102 the system identifies, by analyzing the signals, whether the analyte recovery of the system is meeting a set of conditions where the set of conditions identify a desired analyte recovery of the system. The single analyte may also be converted to plural or multiple analytes. It should be noted that a user of the system may want the recovery of one analyte to be better than the recovery of another analyte, for example, based upon the application, based upon the overall parameter value or composite index, or the like. Thus, the described system and method allows the user to configure the analyte recovery as desired even if the desired configuration of the system is not to provide a maximum or optimal analyte recovery of all analytes within a fluid.

Using the TN and TOC example, the user may choose to have the most efficient $N_2$ recovery, most efficient C recovery, or may choose to have efficient $N_2$ and C recovery. The last option would likely result in an $N_2$ and C recovery that is less than a corresponding analyte associated with one of the first two options. In other words, choosing an efficient $N_2$ and C recovery, would likely result in an $N_2$ recovery less than the $N_2$ recovery in the option where the most efficient $N_2$ recovery was chosen. Based upon the selected recovery options, the system will utilize algorithms that are built into the system to provide the optimal conditions (e.g., temperature, reagent volumes, time, etc.) for achieving the desired recovery option. Thus, the system automates the instrument/system based upon the input taken from the customer to satisfy requirements of the user on a dynamic basis by optimizing the recovery method.

The set of conditions may identify expected responses for the value of the analytes based upon a change in a system parameter, for example, a reagent parameter, a system variable, or the like. In other words, the set of conditions may identify that a particular change (e.g., increase, decrease, maintaining, etc.) in analyte recovery values based upon a known or predetermined system change provides an indication regarding how well the analyte is being recovered. Thus, the set of conditions may provide a type of if/then conditions, which identify that a particular change in analyte value in response to a system change indicates whether the analyte recovery is meeting the desired parameters and, if not, what type of changes needs to be made to the system. Since the described system can provide feedback in real-time, any identification of changes may be compared to previous reaction process values. In other words, the system may store measurement values corresponding to previous reaction process runs and then compare subsequent measurement values to those runs to identify a change in measurement value response.

Figure 2:
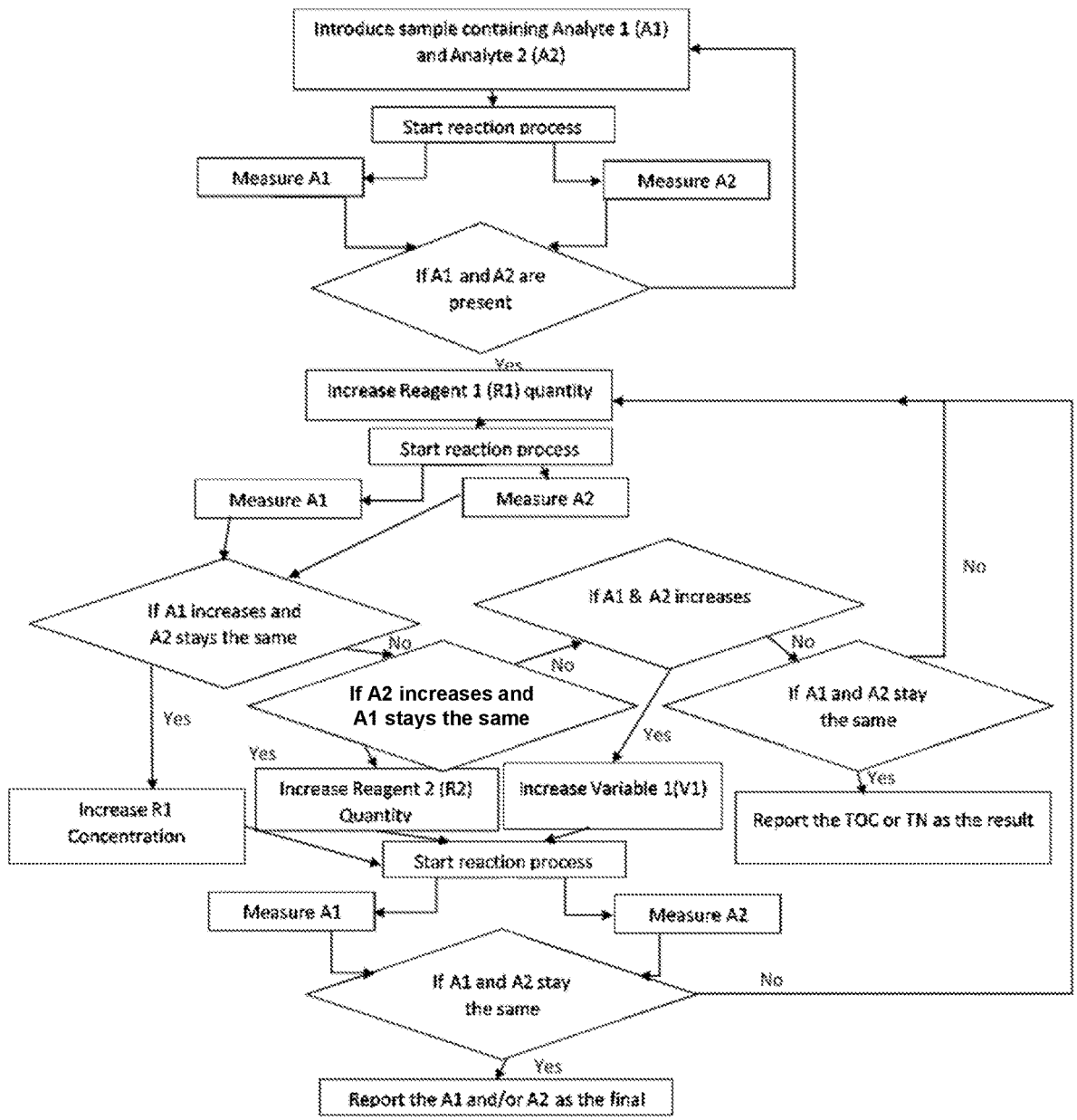
FIG. 2 illustrates an example system diagram of an example embodiment f the described system.

Refer to FIG. 2 as an illustration of an example set of conditions where FIG. 2 also includes an example iteration of the described system and method. The system introduces a fluid or sample that contains analyte 1 (A1), for example, TN in the TN and TOC example, and analyte 2 (A2), for example, TOC in the TN and TOC example, to the measurement system. The reaction process is started where a reagent is introduced to the sample. The system then measures A1 and A2 to determine whether either or both A1 and/or A2 are present within the sample. If A1 and A2 are present, the system increases the quantity of reagent 1 (R1). The reaction process is then restarted using a new portion of the sample containing A1 and A2 and with the new R1 quantity. The system measures A1 and A2 with the new R1 quantity.

If, in response to the increase in R1 quantity, the measurement value A1 is increased and the measurement value of A2 is maintained as compared to the first measurement values, this may indicate that the concentration R1 should be increased. Similarly, if the measurement value of A1 stays the same and the measurement value of A2 increases, this may indicate that a concentration of a second reagent that is different from R1 should be increased. On the other hand, if both A1 and A2 values increase, this may indicate that a different variable V1 of the system should be increased, as discussed in more detail below. If both A1 and A2 measurement values remain the same in response to a change to the change in reagent concentration, the system may determine that the analyte measurement values should be reported. In this example, the analyte measurement values are TOC or TN. Upon making any modifications to the reagent quantity, concentration, or the like, or to another system variable, the system may re-run the reaction process with the modification and determine whether the set of conditions is being met.

As should be understood, the example illustrated in FIG. 2 is merely an example as different sets of conditions can be implemented that identify different conditions and responses. The set of conditions that may be employed may be depend on the application, operating conditions, user desires, and the like. Additionally, different modification responses may be taken in response to the same condition. For example, instead of changing the R1 concentration in response to an increase in A1 value and A2 staying the same, the system may instead change the R1 quantity or a different system variable.

If the analyte recovery of the system is meeting the set of conditions, or a group of set of conditions at 102, the system may report the parameter value from the signal generated from the reaction between the analyte and reagent in the conditions defined by the system at 104. Reporting the analyte measurement value may include correlating the analyte measurement value to a parameter value which is then reported to a user. In other words, the analyte measurement value may not be reported to the user, but rather a derivation of the analyte measurement value may be reported to the user or a different system. For example, instead of reporting the parameter value to the user, the parameter value may be reported to the system for use in determining an overall parameter value, a composite index value, or other multi-parameter value. As indicated above, the parameter value can be derived from or correspond to the analyte measurement value. While the described system may generally relate to a system that provides multi-parameter values, the described system is not so limited. Rather, the described system may also be used in applications where only a single parameter is being measured and/or reported. Even if only a single parameter is being measured, the system may measure multiple analyte values or only a single analyte value.

If, on the other hand, the analyte recovery of the system is not meeting the desired set of conditions at 102, the system may modify the conditions of the system for recovery of the analyte at 103. To modify the conditions and, thereby the analyte recovery, of the system, the system may adjust one or more parameters or variables of the system. Parameters or variables of the system may include reagent parameters, system variables, or the like. Example reagent parameters include reagent concentrations, reagent temperatures, reagent pressure, reagent volumes, reagent quantities, and/or the like. Example system variables include concentration or volumes of buffers, diluents, cleaning solutions, or other fluids, system temperature, activation of a system cleaning cycle, upstream treatment process modifications, and/or the like. It should also be understood that multiple system parameters or variables may be modified in response to the analyte recovery not meeting the desired set of conditions.

As should be understood from the explanation of FIG. 2, the described system and method is an iterative process that can be run and re-run until a desired analyte recovery is achieved, thus optimizing the analyte recovery with respect to the desired analyte recovery. Accordingly, as described in connection with FIG. 2, the system and method may work by starting a reaction process by introducing a fluid sample into the system, identifying analytes are present within the fluid, introducing one or more reagents to the fluid having the analytes, and measuring the analyte value after introduction of the reagent(s). Since the process is iterative, the system may only use a portion of the fluid sample in generating the first analyte measurement value. By only using a portion of the fluid sample, the system can ensure that any changes in analyte measurement values are due to changes to the system parameters or variables and are not due to changes in the fluid. Once changes are made to any system parameters or variables, the reaction process is rerun on a sample of the fluid or portion of the sample of the fluid. A new analyte measurement value is determined using a similar process as described above. This iterative process continues until the analyte recovery meets the desired set of conditions or until a user otherwise stops the process for one reason or another. Thus, the described system and method provides for a real-time feedback loop regarding the analyte recovery of a system which results in more accurate analyte recovery than conventional systems.

Figure 3:
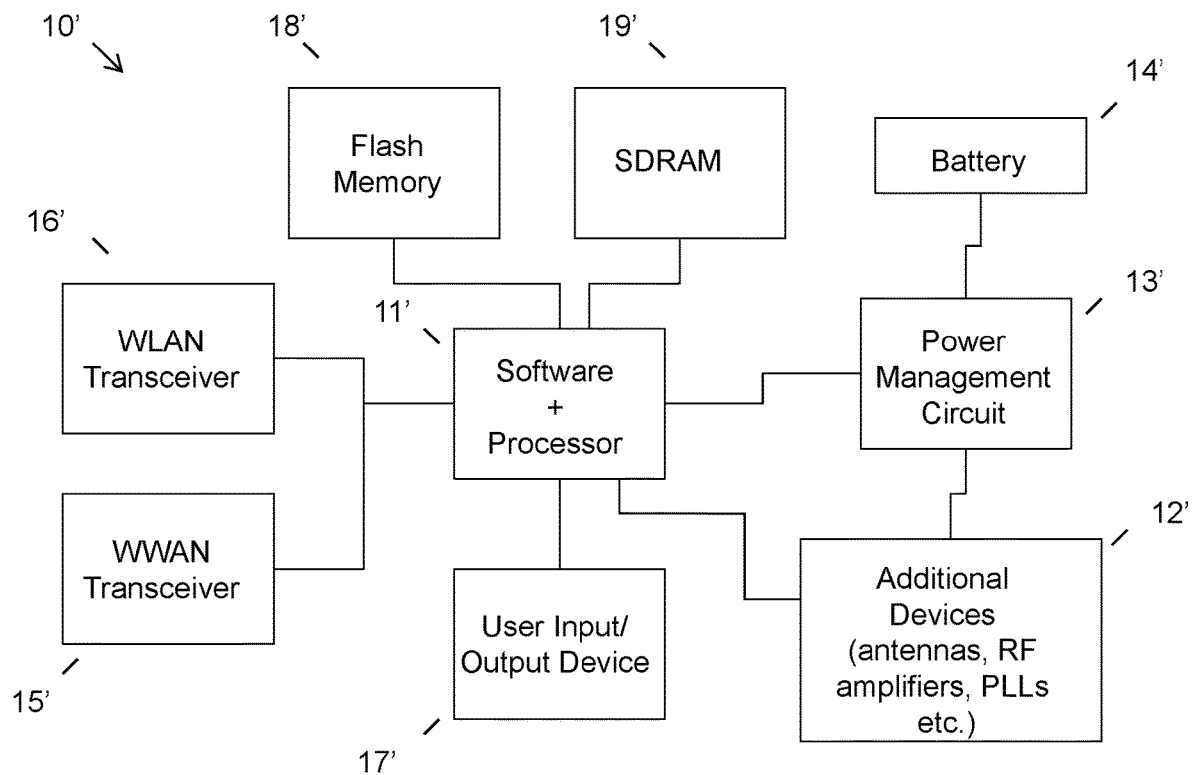
FIG. 3 illustrates an example of computer circuitry.

While various other circuits, circuitry or components may be utilized in information handling devices, with regard to an instrument for alkalinity measurement according to any one of the various embodiments described herein, an example is illustrated in FIG. 3. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'.

Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

Embodiments may be implemented as an instrument, system, method or program product. Accordingly, an embodiment may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

A combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device. For the purpose of this disclosure, a storage medium or device is to be construed as non-transitory, i.e., not inclusive of signals or propagating media.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for real-time management of analyte recovery within a system for measuring at least one parameter of a fluid within the system by monitoring signals from the system against a set of conditions, the method comprising:
receiving, from the system, signals providing information regarding the system, wherein the system comprises at least one reagent flowing into the system and recovers analytes within the fluid, wherein the analytes provide an indication of a value of the at least one parameter;
identifying, by analyzing the signals, whether the analyte recovery of the system is meeting the set of conditions identifying a desired analyte recovery option of the system, wherein the set of conditions comprises an identification of at least one of the analytes for which to optimize recovery; and
modifying, based upon the analyte recovery not meeting the set of conditions and utilizing at least one algorithm identifying conditions of the system for recovery of the at least one of the analytes, a configuration of the system for recovery of the at least one of the analytes, wherein the modifying comprises adjusting at least one parameter of the system.

2. The method of claim 1, wherein the identifying comprises identifying the analyte recovery is not meeting the set of conditions by identifying that a value of at least one of the analytes is increasing and a value of at least another of the analytes is being maintained after increasing a volume of the at least one reagent.

3. The method of claim 2, wherein the adjusting at least one parameter of the system comprises adjusting a parameter of the at least one reagent.

4. The method of claim 1, wherein the identifying comprises identifying the analyte recovery is not meeting the set of conditions by identifying that a value of at least one of the analytes is increasing and a value of at least another of the analytes is increasing after increasing a volume of the at least one reagent.

5. The method of claim 4, wherein the adjusting at least one parameter comprises adjusting a variable of the system.

6. The method of claim 1, wherein the identifying comprises identifying the analyte recovery is meeting the set of conditions by identifying that a value of at least one of the analytes is being maintained and a value of at least another of the analytes is being maintained after increasing a volume of the at least one reagent.

7. The method of claim 6, comprising reporting the at least one parameter derived from the value of the at least one of the analytes and the value of the at least another of the analytes.

8. The method of claim 1, comprising starting a reaction process comprising introducing the fluid to the system, identifying the analytes are present within the fluid, and introducing the at least one reagent to the fluid having the analytes; and
wherein the identifying is responsive to measuring values of the analytes after introduction of the at least one reagent.

9. The method of claim 8, comprising rerunning the reaction process responsive to identifying the analyte recovery is not meeting the set of conditions identified from the measuring of the values and modifying the analyte recovery.

10. The method of claim 1, wherein the system measures a plurality of parameters of the fluid;
wherein the plurality of parameters comprise Total nitrogen and Total organic carbon; and
wherein the set of conditions is selected from the group consisting of: most efficient $N_2$ recovery, most efficient C recovery, and efficient $N_2$ and C recovery.

11. A system for real-time management of analyte recovery within a system for measuring at least one parameter of a fluid within the system by monitoring signals from the system against a set of conditions, the system comprising:
at least one reagent flowing into the system;
a memory storing instructions executable by a processor to:
receive, from the system, signals providing information regarding the system, wherein the system recovers analytes within the fluid, wherein the analytes provide an indication of a value of the at least one parameter;
identify, by analyzing the signals, whether the analyte recovery of the system is meeting the set of conditions identifying a desired analyte recovery option of the system, wherein the set of conditions comprises an identification of at least one of the analytes for which to optimize recovery; and
modify, based upon the analyte recovery not meeting the set of conditions and utilizing at least one algorithm identifying conditions of the system for recovery of the at least one of the analytes, a configuration of the system for recovery of the at least one of the analytes, wherein the modifying comprises adjusting at least one parameter of the system.

12. The system of claim 11, wherein the identifying comprises identifying the analyte recovery is not meeting the set of conditions by identifying that a value of at least one of the analytes is increasing and a value of at least another of the analytes is being maintained after increasing a volume of the at least one reagent.

13. The system of claim 12, wherein the adjusting at least one parameter of the system comprises adjusting a parameter of the at least one reagent.

14. The system of claim 11, wherein the identifying comprises identifying the analyte recovery is not meeting the set of conditions by identifying that a value of at least one of the analytes is increasing and a value of at least another of the analytes is increasing after increasing a volume of the at least one reagent.

15. The system of claim 14, wherein the adjusting at least one parameter comprises adjusting a variable of the system.

16. The system of claim 11, wherein the identifying comprises identifying the analyte recovery is meeting the set of conditions by identifying that a value of at least one of the analytes is being maintained and a value of at least another of the analytes is being maintained after increasing a volume of the at least one reagent.

17. The system of claim 16, comprising reporting the at least one parameter derived from the value of the at least one of the analytes and the value of the at least another of the analytes.

18. The system of claim 11, comprising starting a reaction process comprising introducing the fluid to the system, identifying the analytes are present within the fluid, and introducing the at least one reagent to the fluid having the analytes; and
wherein the identifying is responsive to measuring values of the analytes after introduction of the at least one reagent.

19. The system of claim 18, comprising rerunning the reaction process responsive to identifying the analyte recovery is not meeting the set of conditions identified from the measuring of the values and modifying the analyte recovery.

20. A computer program product for real-time management of analyte recovery within a system for measuring at least one parameter of a fluid within the system by monitoring signals from the system against a set of conditions, the computer program product comprising:
- a storage device having code stored therewith, the code being executable by a processor and comprising:
- code that receives, from the system, signals providing information regarding the system, wherein the system recovers analytes within the fluid, wherein the analytes provide an indication of a value of the at least one parameter;
- code that identifies, by analyzing the signals, whether the analyte recovery of the system is meeting the set of conditions identifying a desired analyte recovery option of the system, wherein the set of conditions comprises an identification of at least one of the analytes for which to optimize recovery; and
- code that modifies, based upon the analyte recovery not meeting the set of conditions and utilizing at least one algorithm identifying conditions of the system for recovery of the at least one of the analytes, a configuration of the system for recovery of the at least one of the analytes, wherein the modifying comprises adjusting at least one parameter of the system.

* * * * *